(12) United States Patent
Wittenbecher et al.

(10) Patent No.: US 8,852,489 B2
(45) Date of Patent: Oct. 7, 2014

(54) PROCESS FOR PREPARING MOLDINGS USING MIXTURES OF AMINES WITH GUANIDINE DERIVATIVES

(75) Inventors: Lars Wittenbecher, Duesseldorf (DE); Michael Henningsen, Frankenthal (DE); Gregor Daun, Neckargemuend (DE); Dieter Flick, Boehl-Iggelheim (DE); Joerg-Peter Geisler, Bingen (DE); Juergen Schillgalies, Moers (DE); Erhard Jacobi, Huenstetten (DE)

(73) Assignee: BASF SE, Ludwigshafen (DE)

( * ) Notice: Subject to any disclaimer, the term of this patent is extended or adjusted under 35 U.S.C. 154(b) by 292 days.

(21) Appl. No.: 13/055,048

(22) PCT Filed: Jul. 17, 2009

(86) PCT No.: PCT/EP2009/059237
§ 371 (c)(1),
(2), (4) Date: Apr. 18, 2011

(87) PCT Pub. No.: WO2010/010047
PCT Pub. Date: Jan. 28, 2010

(65) Prior Publication Data
US 2011/0180970 A1 Jul. 28, 2011

(30) Foreign Application Priority Data

Jul. 22, 2008 (EP) .................................... 08160857
Jul. 8, 2009 (EP) .................... PCT/EP2009/058701

(51) Int. Cl.
*C08J 5/00* (2006.01)
*C07C 279/04* (2006.01)
*C07C 279/16* (2006.01)

(52) U.S. Cl.
CPC ............. *C07C 279/04* (2013.01); *C07C 279/16* (2013.01)
USPC ....................................................... 264/331.12

(58) Field of Classification Search
USPC ....................................................... 264/331.12
See application file for complete search history.

(56) References Cited

U.S. PATENT DOCUMENTS 3,308,094 A 3/1967 Sherr
3,379,591 A 4/1968 Bradley
(Continued)

FOREIGN PATENT DOCUMENTS

CZ 242020 8/1985
DE 10 2005 018 671 A1 10/2006
(Continued)

OTHER PUBLICATIONS

Howard P. Klein, "Huntsman Amine Overview", Huntsman, Beijing Epoxy Conference, Jun. 19, 2007, pp. 1-44.
(Continued)

*Primary Examiner* — Larry Thrower
(74) *Attorney, Agent, or Firm* — Oblon, Spivak, McClelland, Maier & Neustadt, L.L.P.

(57) ABSTRACT

The present invention provides a process for producing moldings, the curing of the mold being carried out using a blend comprising one or more epoxy resins and a mixture, the curing component a) being used within the mixture in the range from 0.3 to 0.9 amine equivalent per equivalent of epoxide of the epoxy resin used, and the hardener component b) being a compound of the formula I.

8 Claims, 2 Drawing Sheets

Diagram 1:
Viscosity rise of the blend in comparison to the prior art at 30°C

(56) References Cited

U.S. PATENT DOCUMENTS

| | | | |
|---|---|---|---|
| 4,269,879 | A | 5/1981 | Davis |
| 4,948,700 | A | 8/1990 | Maeda et al. |
| 5,470,517 | A | 11/1995 | Conley |
| 6,491,845 | B1 | 12/2002 | Schile |
| 6,743,375 | B2 | 6/2004 | Schile |
| 2002/0179240 | A1 | 12/2002 | Clemens et al. |
| 2003/0018131 | A1 | 1/2003 | Davis et al. |
| 2003/0108700 | A1 | 6/2003 | Krech et al. |
| 2004/0059035 | A1 | 3/2004 | Krech et al. |
| 2005/0143496 | A1 | 6/2005 | Mueller |
| 2006/0135706 | A1 | 6/2006 | Davis et al. |

FOREIGN PATENT DOCUMENTS

| | | |
|---|---|---|
| DE | 10 2006 056 311 | 6/2008 |
| EP | 0 659 833 | 6/1995 |
| EP | 1 358 997 | 11/2003 |
| EP | 1 715 003 | 10/2006 |
| JP | 61-83218 | 4/1986 |
| JP | 61-207425 | 9/1986 |
| JP | 2002 187936 | 7/2002 |
| JP | 2002-240205 | 8/2002 |
| JP | 2005-067209 | 3/2005 |
| WO | 02 42349 | 5/2002 |
| WO | 02 070623 | 9/2002 |
| WO | 03 002667 | 1/2003 |
| WO | 03 045801 | 6/2003 |
| WO | 2004 020506 | 3/2004 |
| WO | 2007/107288 | 9/2007 |
| WO | WO 2007/107288 * | 9/2007 |

OTHER PUBLICATIONS

Bruce Burton, et al., "Epoxy Formulations Using Jeffamine® Polyetheramines", Huntsman, Apr. 27, 2005, 105 pages.

"The Jeffamine® Polyetheramines", product specification of Huntsman available from www.huntsman.com, 2007 (6 pages).

Bruce L. Burton, "Amine Curing of Epoxy Resins: Options and Key Formulation Considerations", WWW.PICMAG.COM Huntsman Corp., Jun. 2006 (pp. 68-77).

Allan E. Sherr et al., "Base Catalysts for the Cure of Epoxy Resins", Journal of Applied Polymer Science, vol. 9, 1965 (pp. 2707-2714).

Hexion Specialty Chemicals, "Formulating High Performance Waterborne Epoxy Coatings", 2005 (pp. 1-28).

Goodman, Sidney, "Handbook of Thermoset Plastics", Noyes Publications, 1998 (1 page).

Eberl, Ulrich et al., "Innovative Minds—A Look Inside Siemens' Idea Machine" Publicis KommunikationsAgentur GmbH 2007 (1 page).

Rebecca Dolbey, "RAPRA Review Reports—Expert Overviews covering the Science and Technology of Rubber and Plastics", Rapra Technology Limited, 1997 (1 page).

Henry Lee et al., "Handbook of Epoxy Resins", McGraw-Hill, Inc. 1967 (4 pages).

Derk Visser, "The Annotated European Patent Convention", 2010 (p. 105).

E-Composites, Inc., "Growth Opportunities in Wind Energy Market 2006-2011: Materials, Market and Technologies", 2006 (pp. 198-206).

J Summerscales et al., "Low-pressure (vacuum infusion) techniques for moulding large composite structures", Proc. IMechE, vol. 219, Part L: J. Materials: Design and Applications, Jan. 1, 2005 (pp. 45-58).

English Translation of EP Opposition received in EP 2 307 360 B1 dated Sep. 20, 2012.

Elsevier, Clara D. Craver et al., "Applied Polymer Science", 21st Century Dec. 19, 2000 (English Translatiion).

Becker, Gerhard W. et al. "Kunststoff Handbuch" $2^{nd}$ fully revised edition, 1988 ISBN: 3-446-74418-8.(English Translation).

Stoye, Dieter et al., "Lackharze" (Resins for coatings), Chemistry Properties Application, 1996, ISBN 3-446-17475-3.

S. L. Simon et al. "Reaction Kinetics and TTT Cure Diagrams for Off-Stoichiometric Ratios of a High-$T_g$ Epoxy/Amine System" (Journal of Applied Polymer Science, vol. 46, pp. 1245-1270, Dec. 5, 1992.

Bodo Mueller, et al , "Coatings Formulation" (Vincentz, Coallngs Compendia,., 2006, pp. 110-121, 257, (English Translation).

G. R. Palmese et al., "Effect of Epoxy-Amine Stoichiometry on Cured Resin Material Properties" (Journal of Applied Polymer Science, vol. 46, pp. 1863-1873, Dec. 5, 1992.

English Translation of EP Opposition received in EP 2 307 360, dated Sep. 19, 2012.

International Search Report issued Sep. 10, 2009 in PCT/EP09/059237 filed Jul. 17, 2009.

U.S. Appl. No. 13/054,945, filed Jan. 20, 2011, Wittenbecher, et al.

U.S. Appl. No. 13/055,174, filed Jan. 21, 2011, Daun, et al.

U.S. Appl. No. 13/055,048, filed Jan. 20, 2011, Daun, et al.

* cited by examiner

Figure 1
Diagram 1:
Viscosity rise of the blend in comparison to the prior art at 30°C Figure 2
Diagram 2:
Vitrification time at 70°C

PROCESS FOR PREPARING MOLDINGS USING MIXTURES OF AMINES WITH GUANIDINE DERIVATIVES

The present invention provides a process for producing moldings, the curing of the mold being carried out using a blend comprising one or more epoxy resins and a mixture, the curing component a) being used within the mixture in the range from 0.3 to 0.9 amine equivalent per equivalent of epoxide of the epoxy resin used, and the hardener component b) being a compound of the formula I.

The amine curing of epoxy resins is utilized in a very wide variety of segments. For instance, the amine curing of epoxy resins is employed in the context of adhesives, for the curing of casting resins in special molds, and also for the sealing of surfaces and components to be protected from environmental effects.

One specific, large field of application of the amine curing of epoxy resins is the production of fiber-reinforced plastics. Fiber-reinforced plastics are used as materials of construction for motor vehicles, aircraft, ships and boats, for sports articles and for rotor blades of wind turbines.

The production of large components imposes particular requirements on the hardener or hardener mixture, since during the processing life the viscosity must not rise so sharply that either the fibers are not adequately wetted or else the mold is not completely filled before the epoxy resin becomes no longer processable.

At the same time there ought not to be any adverse effect on the cycle time (processing and curing). Consequently there is a great need for mixtures which are capable of precisely controlling and setting the curing of the epoxy resin in any systems.

H. Klein, in "Huntsman Amine Overview", Huntsman, Jun. 19, 2007, Beijing Epoxy Conference, describes how primary and secondary diamines and polyetheramines can generally be used to cure epoxy resins. A process for producing moldings using a blend in whose mixture the hardener component a) is used in the range from 0.3 to 0.9 amine equivalent, per equivalent of epoxide of the epoxy resin used, and the hardener component b) is a compound of the formula I, is not described, however.

B. Burton, D. Alexander, H. Klein, A. Garibay Vasquez, and C. Henkee, in the product brochure "Epoxy formulations using Jeffamine Polyetheramines", Huntsman, Apr. 21, 2005, describe the stoichiometric use of polyetheramines, or a mixture of polyetheramines and other diamines such as isophoronediamine (IPDA), as a particular form of the amine curing of epoxy resins. The systems in question are two-component systems in which the amine or amine mixture is added to the epoxy resin immediately prior to curing, in amounts which comprise exactly the same number of active amine functions in the amine mixture as there are active epoxide functions in the epoxides.

In hardener formulations comprising polyetheramines and IPDA, the effect of the latter is on the one hand a higher cure rate and on the other hand the observation of higher glass transition temperatures in the cured resins, leading to a higher temperature stability on the part of the cured products—as required for certain applications such as the production of rotor blades, for example—than is the case with curing at comparable temperature using pure polyetheramine.

As compared with the curing of epoxy resins by polyetheramines, however, the addition of IPDA entails not only a higher glass transition temperature on the part of the cured resins but also more rapid curing, which is accompanied by a more rapid increase in viscosity. As a result, the time within which the blend of epoxy resin and hardener/hardener mixture can still be processed is reduced. A disadvantage with hardener mixture systems of this kind, therefore, is that the production of large components, such as rotor blades, is possibly unsuccessful, because the infusion process remains incomplete on account of the development of viscosity.

The rate of the stoichiometric curing of epoxy resins with amines can also be increased by adding tertiary amines to the blend, which function as accelerants. This addition as well leads usually to a more rapid increase in viscosity at room temperature and to shorter pot lives. The pot life or else gelling time is a variable which is commonly utilized to compare the reactivity of different resin/hardener combinations and/or resin/hardener mixture combinations. The measurement of pot life/gelling time (To) is described according to the specification of ASTM D 2471-99 and is a method of characterizing the reactivity of laminating systems by means of a temperature measurement. Depending on application, deviations from the parameters described therein (amount, test conditions, and measurement method) have become established, resulting in a pot life A (ToA) and a pot life B (ToB).

The pot life A (ToA) is determined as follows:

100 g of the blend, comprising epoxy resin and hardener or hardening mixture, are introduced into a container (typically a cardboard carton). A temperature sensor is immersed into this blend, and measures and stores the temperature at defined time intervals. As soon as this blend has solidified, measurement is ended and the time taken to attain the maximum temperature is determined. Where the reactivity of a blend is too low, this measurement is carried out at elevated temperature. As well as the pot life, it is always necessary to report the testing temperature as well.

Pot life B (ToB) is determined as follows:

5 g of the blend comprising epoxy resin and hardener/hardener mixture are introduced in a 5 ml penicillin bottle at a given testing temperature (not adiabatically). A circular die (Ø 11.8 mm) moves up and down (1 mm/sec) in the blend. When a corresponding resistance (about 5 kPa) is reached, the stopwatch is shut off.

Examples of above-described accelerants specified in U.S. Pat. No. 4,948,700, column 10, are triethanolamine, benzyldimethylamine, 2,4,6-tris(dimethylaminomethyl)phenol, and tetramethylguanidine. The fundamental suitability of tetra- and penta-alkylguanidines as hardeners of epoxy resin mixtures is described in U.S. Pat. No. 3,308,094. The use of tetramethylguanidine as a tertiary amine with a very low catalytic activity is also mentioned in U.S. Pat. No. 6,743,375 in column 19. U.S. Pat. No. 6,743,375, however, teaches the skilled worker that tetramethylguanidine is a comparatively slow accelerant. A process for producing moldings using a blend in whose mixture the hardener component a) is used in the range from 0.3 to 0.9 amine equivalent per equivalent of epoxide of the epoxy resin used is not described, however.

Among the technologies employing the curing of epoxides with amines are infusion technologies. In these cases, diepoxy and polyepoxy resins are mixed with amines and polyetheramines immediately prior to the infusion procedure, to form the blend, the blend is drawn into the respective mold under suction, at temperatures of 20° C.-50° C., and is subsequently reacted at molding temperatures of 55° C.-90° C., and the blend is cured as a result. The rate of the overall process is dependent on the duration of the infusion step itself and on the duration of curing. The lower the viscosity of the blend, the quicker the infusion procedure may take place. Reducing the viscosity of a given blend can be accomplished by raising the temperature in the course of the infusion procedure, thereby in principle making it quicker. Raising the temperature during the infusion procedure for the purpose of reducing the viscosity makes sense, however, only with amines of low reactivity, such as polyetheramines, for example. The disadvantage of the sole use of amines of low reactivity, such as polyetheramines, for example, is the slow reaction of this component with the epoxy resin, as a result of which the curing procedure is slow. The duration of curing can be shortened through the use of particularly reactive amines such as IPDA, for example. Where these reactive amines are present, however, infusion must take place at low temperatures, since the viscosity of a mixture of polyetheramine and IPDA at temperatures>40° C. rises so rapidly that it is no longer possible to ensure complete impregnation of the fiber mats.

In the use of infusion technologies such as vacuum assisted resin transfer molding (VARTM) technology for the production of large components, a long pot life on the part of the blend comprising epoxy resins and amines, in the region of several hours at room temperature, may be necessary in order to ensure a trouble-free infusion procedure. This long pot life can be achieved through the use of polyetheramines of low reactivity, as are described in WO-A 2004/020506, pages 14-17. In the state of the art for infusion technology, the exclusive use of active hardeners such as IPDA is unknown for large components. The disadvantage of the use exclusively of polyetheramines of low reactivity in infusion technology lies in the extremely long cure times at elevated temperature, which prevent productivity increase and at the same time necessitate increased employment of energy.

Improvement in the infusion process with blends comprising epoxy resins and amines occurs when the viscosity of the blend during the infusion procedure is low, or when, as a result of a relatively long pot life on the part of the improved blend, the infusion procedure is able to take place at higher temperatures, and hence at a lower viscosity, than is the case for the existing blends of epoxy resins, polyetheramines, and IPDA. The object of an improved process for producing such moldings would be that of exhibiting a comparable or higher cure rate relative to the prior art at temperatures of, for example, 60° C. or more.

Such processes would specifically be very suitable for the manufacture of large components, since, with a comparable or shorter cure rate, the processing time at room temperature would be prolonged, or processing would be possible at higher temperatures, without premature curing of the blend, and hence complete and uniform curing would be enabled.

It is an object of the present invention, therefore, to provide a process for preparing moldings which allows the cure rate of epoxy resins and/or epoxy resin systems to be raised without at the same time increasing the viscosity of the epoxy resin mixture in such a way that complete and uniform curing is no longer possible.

This object is achieved by means of a process for producing moldings, comprising the following steps:
I) providing a mold,
II) introducing a blend comprising one or more epoxy resins and a mixture into the mold according to step I),
III) curing the material present in the mold,
wherein the mixture in step II) comprises a hardener component b) and 0.3 to 0.9 amine equivalent, per equivalent of epoxide of the epoxy resin used in the blend of step II), of a hardener component a),
the hardener component a) comprising one or more amines having a functionality≥2, and at least one amine, when mixed stoichiometrically with the epoxy resin in the 100 g batch, leads at room temperature to a cure time of less than 24 h, and
the hardener component b) comprising at least one compound of the formula I where R1 to R3, R5 and R6 each independently are an organic radical having 1 to 20 C atoms and hydrogen, and R4 is selected from the group of an organic radical having 1 to 20 C atoms and a group —C(NH)NR5R6.

Advantageous is the process of the invention wherein the mold in step I) and/or the blend in step II) comprises reinforcing material, the blend from step II) penetrating the reinforcing material and/or being mixed with it.

Advantageous is the process of the invention wherein the hardener component a) is selected from the group of amines having a functionality≥2.

Advantageous is the process of the invention wherein the hardener component a) comprises at least two hardener components a1) and a2), the hardener component a1) being selected from the group of polyetheramines having a functionality≥2 and the hardener component a2) being selected from the group of further amines having a functionality≥2.

Advantageous is the process of the invention wherein the radicals R1 to R3, R5, and R6 of the compounds of the formula I are each independently selected from the group of hydrogen, methyl, ethyl, n-propyl, isopropyl, n-butyl, sec-butyl, phenyl, and o-tolyl, and R4 is selected from the group of methyl, ethyl, n-propyl, isopropyl, n-butyl, sec-butyl, phenyl, o-tolyl, and a group —C(NH)NR5R6-.

Advantageous is the process of the invention wherein the hardener component b), based on the weight fraction of the mixture in step II), is 5% to 55% by weight.

Advantageous is the process of the invention wherein the mixture of the blend from step II) comprises,
as hardener component a1), a polyetheramine having a functionality≥2 selected from the group of 3,6-dioxa-1,8-octanediamine, 4,7,10-trioxa-1,13-tridecanediamine, 4,7-dioxa-1,10-decanediamine, 4,9-dioxa-1,12-dodecanediamine, polyetheramine based on triethylene glycol with an average molar mass of 148, difunctional, primary polyetheramine prepared by aminating an ethylene glycol grafted with propylene oxide, with an average molar mass of 176, difunctional, primary polyetheramine based on propylene oxide with an average molar mass of 4000, difunctional, primary polyetheramine prepared by aminating a polyethylene glycol grafted with propylene oxide, with an average molar mass of 2003, aliphatic polyetheramine based on polyethylene glycol grafted with propylene oxide, with an average molar mass of 900, aliphatic polyetheramine based on polyethylene glycol grafted with propylene oxide, with an average molar mass of 600, difunctional, primary polyetheramine prepared by aminating a diethylene glycol grafted with propylene oxide, with an average molar mass of 220, aliphatic polyetheramine based on a copolymer of poly(tetramethylene ether glycol) and polypropylene glycol with an average molar mass of 1000, aliphatic polyetheramine based on a copolymer of poly(tetramethylene ether glycol) and polypropylene glycol with an average molar mass of 1900, aliphatic polyetheramine based on a copolymer of poly(tetramethylene ether glycol) and polypropylene glycol with an average molar mass of 1400, polyethertriamine based on an at least trihydric alcohol grafted with butylene oxide, with an average molar mass of 400, aliphatic polyetheramine prepared by aminating alcohols grafted with butylene oxide, with an average molar mass of 219, polyetheramine based on pentaerythritol and propylene oxide with an average molar mass of 600, difunctional, primary polyetheramine based on polypropylene glycol with an average molar mass of 2000, difunctional, primary polyetheramine based on polypropylene glycol with an average molar mass of 230, difunctional, primary polyetheramine based on polypropylene glycol with an average molar mass of 400, trifunctional, primary polyetheramine prepared by reacting propylene oxide with trimethylolpropane, followed by amination of the terminal OH groups, with an average molar mass of 403, trifunctional, primary polyetheramine prepared by reacting propylene oxide with glycerol, followed by amination of the terminal OH groups, with an average molar mass of 5000, and a polyetheramine having an average molar mass of 400, prepared by aminating polyTHF which has an average molar mass of 250, as hardener component a2), a further amine having a functionality≥2 selected from the group of 1,12-diaminododecane, 1,10-diamino-decane, 1,2-diaminocyclohexane, 1,2-propanediamine, 1,3-bis(aminomethyl)cyclohexane, 1,3-propanediamine, 1-methyl-2,4-diaminocyclohexane, 2,2'-oxybis(ethylamine), 3,3'-dimethyl-4,4'-diaminodicyclohexylmethane, 4,4'-methylenedianiline, 4-ethyl-4-methylamino-1-octylamine, diethylenetriamine, ethylenediamine, hexamethylenediamine, isophoronediamine, menthenediamine, xylylenediamine, N-aminoethylpiperazine, neopentanediamine, norbornanediamine, octamethylene-diamine, piperazine, 4,8-diaminotricyclo[5.2.1.0]decane, tolylenediamine, triethylenetetramine, and trimethylhexamethylenediamine, and as hardener component b), 5% to 55% by weight of the compound of the formula I, based on the mixture, the ratio of a1) to a2) being in the range from 0.1 to 10:1.

Advantageous is the process of the invention wherein as hardener component a1) a polyetheramine having a functionality of ≥2 is used, selected from the group of difunctional, primary polyetheramine prepared by aminating a diethylene glycol grafted with propylene oxide, with an average molar mass of 220, aliphatic polyetheramine based on polyethylene glycol grafted with propylene oxide, with an average molar mass of 900, aliphatic polyetheramine based on a copolymer of poly(tetramethylene ether glycol) and polypropylene glycol, with an average molar mass of 1000, aliphatic polyetheramine based on a copolymer of poly(tetramethylene ether glycol) and polypropylene glycol, with an average molar mass of 1900, aliphatic polyetheramine based on a copolymer of poly(tetramethylene ether glycol) and polypropylene glycol, with an average molar mass of 1400, polyethertriamine based on an at least trihydric alcohol grafted with butylene oxide, with an average molar mass of 400, aliphatic polyetheramine prepared by aminating alcohols grafted with butylene oxide, with an average molar mass of 219, difunctional, primary polyetheramine based on polypropylene glycol, with an average molar mass of 230, difunctional, primary polyetheramine based on polypropylene glycol, with an average molar mass of 400, trifunctional, primary polyetheramine prepared by reacting propylene oxide with trimethylolpropane, followed by amination of the terminal OH groups, with an average molar mass of 403, and polyetheramine based on propylene oxide and glycerol, with an average molar mass of 5000.

Advantageous is the process of the invention wherein as hardener component a1) a polyetheramine selected from the group of polyetheramine D 230, polyetheramine D 400, polyetheramine T 403 and polyetheramine T 5000 is used, and as a further amine hardener component a2) is used selected from the group of isophoronediamine, aminoethylpiperazine, 1,3-bis(aminomethyl)cyclohexane, and triethylenetetraamine is used, and as hardener component b) tetramethylguanidine is used.

The blends of the invention comprise at least one and/or two or more epoxy resins and a mixture of a hardener component a) and a hardener component b). The epoxy resins and/or epoxy resin mixtures for use preferably comprise epoxy resins selected from the group of bisphenol A bisglycidyl ether (DGEBA), bisphenol F bisglycidyl ether, bisphenol S bisglycidyl ether (DGEBS), tetraglycidylmethylenedianilines (TGMDA), epoxy novolaks (the reaction products of epichlorohydrin and phenolic resins (novolak)), and cycloaliphatic epoxy resins such as 3,4-epoxycyclohexylmethyl 3,4-epoxycyclohexanecarboxylate and diglycidyl hexahydrophthalate.

Moreover the epoxy resins may also comprise further reactive diluents. These diluents are selected from the group of 1,4-butanediol bisglycidyl ether, 1,6-hexanediol bis-glycidyl ether, glycidyl neodecanoate, glycidyl versatate, 2-ethylhexyl glycidyl ether, $C_8$-$C_{10}$ alkyl glycidyl ethers, $C_{12}$-$C_{14}$ alkyl glycidyl ethers, p-tert-butyl glycidyl ether, butyl glycidyl ether, nonylphenyl glycidyl ether, p-tert-butylphenyl glycidyl ether, phenyl glycidyl ether, o-cresyl glycidyl ether, polyoxypropylene glycol diglycidyl ether, trimethylolpropane triglycidyl ether (TMP), glycerol triglycidyl ether, and triglycidyl-para-aminophenol (TGPAP).

In accordance with the prior art a virtually stoichiometric amount is used for the curing of epoxy resins (depending on epoxy resin, 0.9-1.1 equivalents of the hardener/equivalent of epoxy resin). If, however, the mixture of the invention is used for curing epoxy resins, it is preferred to add 10 to 60 mol %, more preferably 20 to 40 mol %, less of the inventive mixture to the epoxy resin than needed for the reaction of the active epoxy groups at amine functions of the mixture. It is particularly preferred if, in total, 0.3 to 0.9 amine equivalent, preferably 0.4 to 0.7 amine equivalent, per epoxide equivalent of the epoxy resin used, of hardener components a1) and a2) is added to the mixture in order to obtain an increase in the pot life and a comparable or improved curing of the epoxy resin as compared with the mixtures of the prior art. For the blend of the invention the fraction of the hardener component a) is 0.3 to 0.9, preferably 0.4 to 0.7, amine equivalent per epoxide equivalent of the epoxy resin used. For preparing the blend of the invention and for the process of the invention, the mixture is mixed with the epoxy resin at temperatures below the initial curing temperature of the hardener component a). The initial curing temperature is the temperature at which, in a mixture of two or more hardener components having a functionality≥2, the first hardener component reacts with the epoxy resin. This temperature can be determined by a DSC in accordance with DIN 53765 as $TRO^E$.

The hardener component a) in the blend of the invention, and also for the process of the invention, comprises one or more amines having a functionality≥2, at least one amine, when mixed stoichiometrically with the epoxy resin in the 100 g batch, leading at room temperature to a cure time of less than 24 h.

The amines having a functionality≥2 of hardener component a) are all amines known to the skilled worker and having a functionality≥2. Preferably they are selected from the group of 3,6-dioxa-1,8-octanediamine, 4,7,10-trioxa-1,13-tridecanediamine, 4,7-dioxa-1,10-decanediamine, 4,9-dioxa-1,12-dodecanediamine, polyetheramine based on triethylene glycol with an average molar mass of 148, difunctional, primary polyetheramine prepared by aminating an ethylene glycol grafted with propylene oxide, with an average molar mass of 176, difunctional, primary polyetheramine based on propylene oxide with an average molar mass of 4000, difunctional, primary polyetheramine prepared by aminating a polyethylene glycol grafted with propylene oxide, with an average molar mass of 2003, aliphatic polyetheramine based on polyethylene glycol grafted with propylene oxide, with an average molar mass of 900, aliphatic polyetheramine based on polyethylene glycol grafted with propylene oxide, with an average molar mass of 600, difunctional, primary polyetheramine prepared by aminating a diethylene glycol grafted with propylene oxide, with an average molar mass of 220, aliphatic polyetheramine based on a copolymer of poly(tetramethylene ether glycol) and polypropylene glycol with an average molar mass of 1000, aliphatic polyetheramine based on a copolymer of poly(tetramethylene ether glycol) and polypropylene glycol with an average molar mass of 1900, aliphatic polyetheramine based on a copolymer of poly(tetramethylene ether glycol) and polypropylene glycol with an average molar mass of 1400, polyethertriamine based on an at least trihydric alcohol grafted with butylene oxide, with an average molar mass of 400, aliphatic polyetheramine prepared by aminating alcohols grafted with butylene oxide, with an average molar mass of 219, polyetheramine based on pentaerythritol and propylene oxide with an average molar mass of 600, difunctional, primary polyetheramine based on polypropylene glycol with an average molar mass of 2000, difunctional, primary polyetheramine based on polypropylene glycol with an average molar mass of 230, difunctional, primary polyetheramine based on polypropylene glycol with an average molar mass of 400, trifunctional, primary polyetheramine prepared by reacting propylene oxide with trimethylolpropane, followed by amination of the terminal OH groups, with an average molar mass of 403, trifunctional, primary polyetheramine prepared by reacting propylene oxide with glycerol, followed by amination of the terminal OH groups, with an average molar mass of 5000, and a polyetheramine having an average molar mass of 400, prepared by aminating polyTHF which has an average molar mass of 250, 1,12-diaminododecane, 1,10-diaminodecane, 1,2-diaminocyclohexane, 1,2-propanediamine, 1,3-bis(aminomethyl)cyclohexane, 1,3-propanediamine, 1-methyl-2,4-diaminocyclohexane, 2,2'-oxybis(ethylamine), 3,3'-dimethyl-4,4'-diaminodicyclohexylmethane, 4-ethyl-4-methylamino-1-octylamine, diethylenetriamine, ethylenediamine, hexamethylenediamine, isophoronediamine, menthenediamine, xylylenediamine, N-aminoethylpiperazine, neopentanediamine, norbornanediamine, octamethylenediamine, piperazine, 4,8-diaminotricyclo[5.2.1.0]decane, tolylenediamine, triethylenetetramine, and trimethylhexamethylenediamine.

With particular preference the hardener component a) comprises at least two hardener components a1) and a2), with both comprising an amine having a functionality≥2. With very particular preference the hardener component a1) comprises a polyetheramine and the hardener component a2) comprises a further amine having a functionality≥2.

Polyamines with oxygen in their chain are referred to as polyetheramines.

Polyetheramines having a functionality of ≥2 can be used in the blend of the invention and in the process of the invention as hardener component a), and in the mixture of the invention as hardener component a1). They can be prepared inter alia on the basis of alkylene oxides such as ethylene oxide, propylene oxide, butylene oxide or pentylene oxide, polyTHF or 1,4-butanediol and in each case ammonia, and have molar weight distributions. The alkylene oxides used may be the same or different per molecule. The polyetheramines of types D, ED, and EDR are diamines (D type), with ED standing for diamine based on polyethylene glycol (PEG) and EDR standing for reactive diamines based on PEG; the T types are a triol which is grafted with alkylene oxide(s) and which carries an amino group on each of the three termini. XTJ is used for products still intended for trial. The numbers after the letter code, except for the XTJ products, in the name of the polyetheramines gives the average molar mass of the polyetheramine. The polyetheramines used in the mixture of the invention, in the blend of the invention, and in the process of the invention have a functionality of ≥2.

Typical examples of polyetheramines of hardener component a1) are selected from the group of difunctional, primary polyetheramine based on polypropylene glycol, with an average molar mass of 230, difunctional, primary polyetheramine based on polypropylene glycol, with an average molar mass of 400, difunctional, primary polyetheramine based on polypropylene glycol, with an average molar mass of 2000, difunctional, primary polyetheramines based on propylene oxide, with an average molar mass of 4000, trifunctional, primary polyetheramine prepared by reacting propylene oxide with trimethylolpropane, followed by amination of the terminal OH groups, with an average molar mass of 403, trifunctional, primary polyetheramine prepared by reacting propylene oxide with glycerol, followed by amination of the terminal OH groups, with an average molar mass of 5000. These compounds are also sales products of the companies BASF (Polyetheramines) and Huntsman (Jeffamines) and are available under the following tradenames:

Polyetheramine D 230/Jeffamine® D 230:
comprises polyetheramine based on polypropylene glycol with an average molar mass of 230.

Polyetheramine D 400/Jeffamine® XTJ 582:
comprises difunctional, primary polyetheramine based on polypropylene glycol with an average molar mass of 400.

Polyetheramine D 2000/Jeffamine® D2000/Jeffamine® XTJ 578:
comprises aliphatic, difunctional, primary polyetheramine based on polypropylene glycol with an average molar mass of 2000.

Polyetheramine D 4000:
comprises polyetheramines based on polypropylene glycol with an average molar mass of 4000.

Polyetheramine T 403/Jeffamine® T 403:
comprises polyetheramine prepared by reacting propylene oxide with trimethylolpropane, followed by amination of the terminal OH groups, with an average molar mass of 403.

Polyetheramine T 5000/Jeffamine® T 5000:
comprises polyetheramine prepared by reacting propylene oxide with glycerol, followed by amination of the terminal OH groups, with an average molar mass of 5000.

Jeffamine® ED-600/Jeffamine® XTJ 501:
comprises an aliphatic polyetheramine constructed from a polyethylene glycol grafted with propylene oxide, and having an average molar mass of 600.

Jeffamine® ED-900:
comprises an aliphatic polyetheramine constructed from a polyethylene glycol grafted with propylene oxide, and having an average molar mass of 900.

Jeffamine® ED-2003:
comprises an aliphatic polyetheramine constructed from a polyethylene glycol grafted with propylene oxide, and having an average molar mass of 2000.

Jeffamine® HK-511:
comprises a difunctional, primary polyetheramine prepared by aminating a diethylene glycol capped with propylene oxide, with an average molar mass of 220.

Jeffamine® XTJ-542:
comprises an aliphatic polyetheramine based on a copolymer of poly(tetramethylene ether glycol) and polypropylene glycol, with an average molar mass of 1000.

Jeffamine® XTJ-548:
comprises an aliphatic polyetheramine based on a copolymer of poly(tetramethylene ether glycol) and polypropylene glycol, with an average molar mass of 1900.

Jeffamine® XTJ-559:
comprises copolymers of poly(tetramethylene ether glycol) and polypropylene glycol with an average molar mass of 1400.

Jeffamine® XTJ-566:
comprises polyethertriamine based on an at least trihydric alcohol grafted with butylene oxide, with an average molar mass of 400.

Jeffamine® XTJ-568:
comprises an aliphatic polyetheramine prepared by aminating alcohols grafted with butylene oxide, with an average molar mass of 219.

Jeffamine® XTJ-616:
comprises a polyetheramine based on pentaerythritol and propylene oxide with an average molar mass of 600.

Jeffamine® EDR-148:
comprises a polyetheramine based on triethylene glycol with an average molar mass of 148.

Jeffamine® EDR-176:
comprises a difunctional, primary polyetheramine prepared by aminating an ethylene glycol capped with propylene oxide, with an average molar mass of 176.

PolyTHF-Amine 350:
comprises a polyetheramine prepared by aminating polyTHF with an average molar mass of 250. The resultant polyTHF-amine possesses an average molecular weight of 400.

The polyetheramines of hardener component a1) are preferably selected from the group of difunctional, primary polyetheramine prepared by aminating diethylene glycol, grafted with propylene oxide, with an average molar mass of 220, aliphatic polyetheramine based on polyethylene glycol grafted with propylene oxide, with an average molar mass of 900, aliphatic polyetheramine based on a copolymer of poly(tetramethylene ether glycol) and polypropylene glycol with an average molar mass of 1000, aliphatic polyetheramine based on a copolymer of poly(tetramethylene ether glycol) and polypropylene glycol with an average molar mass of 1900, aliphatic polyetheramine based on a copolymer of poly(tetramethylene ether glycol) and polypropylene glycol with an average molar mass of 1400, polyethertriamine based on an at least trihydric alcohol grafted with butylene oxide, with an average molar mass of 400, aliphatic polyetheramine prepared by aminating alcohols capped with butylene oxide, with an average molar mass of 219, difunctional, primary polyetheramine based on polypropylene glycol with an average molar mass of 230, difunctional, primary polyetheramine based on polypropylene glycol with an average molar mass of 400, trifunctional, primary polyetheramine prepared by reacting propylene oxide with trimethylolpropane, followed by amination of the terminal OH groups, with an average molar mass of 403, and a polyetheramine based on propylene oxide and glycerol with an average molar mass of 5000. A very particularly preferred polyetheramine is a polyetheramine based on polypropylene glycol with an average molar mass of 230, such as polyetheramine D 230 or Jeffamine® D230, for example.

Hardener components a2) used are further amines having a functionality≥2, selected from the group of 1,12-diaminododecane, 1,10-diaminodecane, 1,2-diaminocyclohexane, 1,2-propanediamine, 1,3-bis(aminomethyl)cyclohexane, 1,3-propanediamine, 1-methyl-2,4-diaminocyclohexane, 2,2'-oxybis(ethylamine), 3,3'-dimethyl-4,4'-diaminodicyclohexylmethane, 4,4'-methylenedianiline, 4-ethyl-4-methylamino-1-octylamine, diethylenetriamine, ethylenediamine, hexamethylenediamine, isophoronediamine, menthenediamine, xylylenediamine, N-aminoethylpiperazine, neopentanediamine, norbornanediamine, octamethylenediamine, piperazine 4,8-diaminotricyclo[5.2.1.0]-decane, tolylenediamine, triethylenetetramine, and trimethylhexamethylenediamine.

In the mixture of the invention, the blend of the invention and also in the process of the invention there may also be accelerants present as well. These are selected from the group of substituted imidazoles such as 1-methylimidazole, 2-methylimidazole, 2-ethyl-4-methylimidazole, 2-phenylimidazole, 1-cyanoethylimidazole, imidazolines such as 2-phenylimidazoline, tertiary amines such as N,N-dimethylbenzylamine, 2,4,6-tris(dimethylaminomethyl)phenol (DMP 30), bisphenol A, bisphenol F, nonylphenol, p-tert-butylphenol, phenolic resins of the novolak type, salicylic acid, p-toluenesulfonic acid, 1,4-diazabicyclo[2.2.2]octane (DABCO), 1,8-diazabicyclo[5.4.0]undec-7-ene (DBU), S-triazine (Lupragen N 600), bis(2-dimethylaminoethyl) ether (Lupragen N 206), pentamethyldiethylenetriamine (Lupragen N 301), trimethylaminoethylethanolamine (Lupragen N 400), tetramethyl-1,6-hexanediamine (Lupragen N 500), aminoethylmorpholine, aminopropylmorpholine, aminoethylethyleneurea, ketimines such as Epi-Kure 3502 (a reaction product of ethylenediamine with methyl isobutyl ketone), urons such as 3-(4-chlorophenyl)-1,1-dimethylurea (Monuron), 3-(3,4-dichlorophenyl)-1,1-dimethylurea (Diuron), 3-phenyl-1,1-dimethylurea (Fenuron), and 3-(3-chloro-4-methylphenyl)-1,1-dimethylurea (Chlorotoluron), tolyl-2,4 bis-N,N-dimethylcarbamide (Amicure UR2T), dicyandiamide (DICY), Mannich bases or secondary amines such as dialkylamines, such as di(2-ethylhexyl)amine, dibutylamine, dipropylamine, ditridecylamine, N,N'-diisopropylisophoronediamine (Jefflink® XTJ-584), N,N'-diisobutyl-4,4"-diaminodicyclohexylmethane (Clearlink 1000), N-(hydroxyethyl)aniline, and di(2-methoxyethyl)amine, for example.

In addition to the hardener component a) or a1) and a2), the mixture of the invention, the blend of the invention and the process of the invention further comprise a hardener component b) of the formula I (I)

The radicals R1 to R3, R5, and R6 of the formula I in the hardener component b) of the mixture of the invention, of the blend of the invention and also of the process of the invention are each independently selected from the group of an organic radical having 1 to 20 C atoms and hydrogen. Organic radical means all saturated, unsaturated, cyclic or acyclic hydrocarbon radicals which carry no heteroatoms. With particular preference the organic radical has 1 to 10 C atoms.

Organic radicals which are unsaturated and cyclic include aromatic groups. Preferred aromatic hydrocarbon radicals are selected from the group of phenyl, benzyl, xylene, o-tolyl, a phenyl group substituted by one or more $C_2$ to $C_4$ alkyl groups, and benzyl group. Particularly preferred aromatic hydrocarbon radicals are phenyl groups. The aliphatic hydrocarbon radicals are selected from the group of cyclic and acyclic hydrocarbon radicals. The acyclic aliphatic hydrocarbon radicals are preferred. In this case it is possible with preference, as hydrocarbon radicals, to use those with $C_1$ to $C_{10}$ atoms, more preferably $C_1$ to $C_4$ atoms.

With very particular preference the radicals for R1 to R3, R5, and R6 are selected from the group of methyl, ethyl, n-propyl, isopropyl, n-butyl, sec-butyl, phenyl, and o-tolyl radicals. With very particular preference more particularly, the radicals selected for the radicals R1 to R3, R5 and R6 are the aliphatic hydrocarbon radicals selected from the group of methyl, ethyl, n-propyl, isopropyl, n-butyl or sec-butyl group. With very particular preference more particularly are methyl, ethyl, n-propyl, and n-butyl group. R4, for the mixture of the invention, the blend of the invention and the process of the invention, is selected, independently of R1 to R3, R5, and R6, from the group of an organic radical having 1 to 20 C atoms and a group —C(NH)NR5R6-. With particular preference R4 is selected from the group of methyl, ethyl, n-propyl, isopropyl, n-butyl, sec-butyl, phenyl and o-tolyl radical. With very particular preference more particularly are methyl, ethyl, n-propyl, n-butyl, and o-tolyl radical.

In one particularly preferred embodiment R1 to R4 independently of one another are organic aliphatic hydrocarbons selected from the group of methyl, ethyl, n-propyl, isopropyl, n-butyl, and sec-butyl radical. With very particular preference more particularly are methyl, ethyl, n-propyl, and n-butyl group.

With very particular preference more particularly the compound of formula I is tetramethylguanidine.

The fraction of the compound of the formula I in the blend of the invention and in the process of the invention is situated in the range from 0.5% to 25% by weight, based on the amount of epoxy resin used.

The fraction of the formula I in the mixture of the invention is situated in the range from 5% to 55%, preferably in the range from 5% to 30%, more preferably between 10% and 25%, by weight, based on the amount of the mixture.

Preferred mixtures of the invention and also blends of the invention are those which in addition to tetramethylguanidine also, additionally, comprise polyetheramines selected from the group of 3,6-dioxa-1,8-octanediamine, 4,7,10-trioxa-1, 13-tridecanediamine, 4,7-dioxa-1,10-decanediamine, 4,9-dioxa-1,12-dodecanediamine, difunctional, primary polyetheramine based on polypropylene glycol with an average molar mass of 2000, such as, for example, Jeffamine® D-2000, Jeffamine® XTJ-578 and Polyetheramine D 2000, difunctional, primary polyetheramine based on polypropylene glycol with an average molar mass of 230, such as, for example, Jeffamine® D-230 and Polyetheramine D 230, difunctional, primary polyetheramine based on polypropylene glycol with an average molar mass of 400, such as, for example, Jeffamine® D-400, Jeffamine® XTJ-582 and Polyetheramine D 400, difunctional, primary polyetheramine based on propylene oxide with an average molar mass of 4000, such as, for example, Jeffamine® D-4000, difunctional, primary polyetheramine prepared by aminating a polyethylene glycol grafted with propylene oxide, with an average molar mass of 2003, such as, for example, Jeffamine® ED-2003, aliphatic polyetheramine based on polyethylene glycol grafted with propylene oxide, with an average molar mass of 900, such as, for example, Jeffamine® ED-900, aliphatic polyetheramine based on polyethylene glycol grafted with propylene oxide, with an average molar mass of 2000, such as, for example, Jeffamine® ED-2003, aliphatic polyetheramine based on polyethylene glycol grafted with propylene oxide, with an average molar mass of 600, such as, for example, Jeffamine® ED-600 and Jeffamine® XTJ 501, difunctional, primary polyetheramine prepared by aminating a diethylene glycol grafted with propylene oxide, with an average molar mass of 220, such as, for example, Jeffamine® HK-511, trifunctional, primary polyetheramine prepared by reacting propylene oxide with trimethylolpropane, followed by amination of the terminal OH groups, with an average molar mass of 403, such as, for example, Jeffamine® T-403 and Polyetheramine T 403, trifunctional, primary polyetheramine prepared by reacting propylene oxide with glycerol, followed by amination of the terminal OH groups, with an average molar mass of 5000, such as, for example, Jeffamine® T-5000 and Polyetheramine T 5000, aliphatic polyetheramine based on a copolymer of poly(tetramethylene ether glycol) and polypropylene glycol with an average molar mass of 1000, such as, for example, Jeffamine® XTJ-542, aliphatic polyetheramine based on a copolymer of poly(tetramethylene ether glycol) and polypropylene glycol with an average molar mass of 1900, such as, for example, Jeffamine® XTJ-548, aliphatic polyetheramine based on a copolymer of poly(tetramethylene ether glycol) and polypropylene glycol with an average molar mass of 1400, such as, for example, Jeffamine® XTJ-559, aliphatic polyethertriamine based on an at least trihydric alcohol grafted with butylene oxide, with an average molar mass of 400, such as, for example, Jeffamine® XTJ-566, aliphatic polyetheramine prepared by aminating alcohols grafted with butylene oxide, with an average molar mass of 219, such as, for example, Jeffamine® XTJ-568, polyetheramine based on pentaerythritol and propylene oxide with an average molar mass of 600, such as, for example, Jeffamine® XTJ-616, polyetheramine based on triethylene glycol with an average molar mass of 148, such as, for example, Jeffamine® EDR 148, difunctional, primary polyetheramine prepared by aminating an ethylene glycol grafted with propylene oxide, with an average molar mass of 176, such as, for example, Jeffamine® EDR 176; and a polyetheramine having an average molar mass of 400, prepared by aminating polyTHF with an average molar mass of 250, such as polyTHF Amine 350, for example.

Particularly preferred mixtures of the invention and also blends of the invention are firstly those which besides tetramethylguanidine and polyetheramines selected from the group of difunctional, primary polyetheramine based on polypropylene glycol with an average molar mass of 230, such as, for example, Jeffamine® D-230 and Polyetheramine D 230, difunctional, primary polyetheramine based on polypropylene glycol with an average molar mass of 400, such as, for example, Jeffamine® D-400, Jeffamine® XTJ-582, and Polyetheramine D 400, difunctional, primary polyetheramine prepared by aminating a diethylene glycol grafted with propylene oxide, with an average molar mass of 220, such as, for example, Jeffamine® HK-511, trifunctional, primary polyetheramine prepared by reacting propylene oxide with trimethylolpropane, followed by amination of the terminal OH groups, with an average molar mass of 403, such as, for example, Jeffamine® T-403 and Polyetheramine T 403, aliphatic polyetheramine based on polyethylene glycol grafted with propylene oxide, with an average molar mass of 900, such as, for example, Jeffamine® ED-900, aliphatic polyetheramine based on a copolymer of poly(tetramethylene ether glycol) and polypropylene glycol with an average molar mass of 1000, such as, for example, Jeffamine® XTJ-542, polyetheramine based on a copolymer of poly(tetramethylene ether glycol) and polypropylene glycol with an average molar mass of 1900, such as, for example, Jeffamine® XTJ-548, aliphatic polyetheramine based on a copolymer of poly(tetramethylene ether glycol) and polypropylene glycol with an average molar mass of 1400, such as, for example, Jeffamine® XTJ-559, aliphatic polyethertriamine based on an at least trihydric alcohol grafted with butylene oxide, with an average molar mass of 400, such as, for example, Jeffamine® XTJ-566, aliphatic polyetheramine prepared by aminating alcohols grafted with butylene oxide, with an average molar mass of 219, such as, for example, Jeffamine® XTJ-568, also, additionally, comprise a diamine selected from the group of isophoronediamine, 1,2-diaminocyclohexane, 1-methyl-2,4-diaminocyclohexane, and 1,3-bis(aminomethyl)cyclohexane. A very particularly preferred mixture of the invention is the mixture comprising tetramethylguanidine, difunctional primary polyetheramine based on polypropylene glycol with an average molar mass of 230, such as, for example, Jeffamine® D-230 and Polyetheramine D 230 and isophoronediamine.

In the case of a mixture of the invention and of a preferred blend of the invention in which, in addition to the compound of the formula I, a polyetheramine and a further amine having a functionality≥2 are used, the polyetheramine is present in a ratio with respect to the further amine in the range from 0.1 to 10:1, preferably in the range from 1.5 to 10:1, more preferably in the range from 2.0 to 5.0:1. In an especially preferred mixture of the invention and a more particularly especially preferred blend comprising tetramethylguanidine, Polyetheramine D230/Jeffamine® D230, and isophoronediamine, the preferred mixing ratio of Polyetheramine D230/Jeffamine® D230 to isophoronediamine is in the range from 2.2 to 2.6:1, more preferably in the range from 2.3 to 2.5:1.

The mixture of the invention is mixed from the individual constituents by mechanical methods known to the skilled worker at temperatures below 160° C., preferably in the range from 5 to 30° C.

When the mixture of the invention is utilized to cure epoxy resins, the rate of curing is comparable or better in relation to curing systems from the prior art.

Besides the use of the mixture of the invention in infusion technologies such as, for example, resin infusion, resin transfer molding (RTM), vacuum assisted resin transfer molding (VARTM), which are described in U.S. Pat. No. 3,379,591, the mixtures of the invention and blends of the invention can also be employed for further technologies for the curing of epoxy resins that require a sufficient processing life at temperatures of 15-45° C. in combination with rapid curing at higher temperatures. These technologies are selected from the group of filament winding, pultrusion, hand lay-up and prepreg, as described in U.S. Pat. Nos. 3,379,591 and 5,470,517. In the hand lay-up process, a fiber material is wetted manually or mechanically with epoxy resin and then these mats are inserted into a mold and, where two or more layers are used, are consolidated with rollers or similar apparatus. Curing often takes place in a vacuum bag, since this consolidates the material and allows a precise epoxy resin content to be set.

The present invention further provides the cured epoxy resin obtainable by curing the blend of the invention or by curing an epoxy resin or epoxy resin mixture with the mixture of the invention. For this purpose the blends of the invention are either introduced into special molds or applied to surfaces and induced to cure by an increase in temperature. The blends for application to surfaces may further comprise additional fillers in the blends. These fillers are selected from the group of thixotropic agents (hydrophilic and hydrophobic fumed silicas), UV stabilizers (nanoscale oxides such as titanium dioxide and zinc oxide), flame retardants (polyphosphates and phosphorus), silicates, and carbonates for improving the mechanical properties. The molds that are used and into which the blends of the invention are introduced may comprise fiber-reinforcing material or else may comprise elements which are to be protected from environmental effects such as damp, oxygen, dust particles or other aggressive materials or influences.

Preferred cured epoxy resins are those which are cured in a molding. These moldings are selected from the group of moldings for motor vehicles, aircraft, ships, boats, sports goods, and blades for wind turbines. Moldings for rotor blades of wind turbines are particularly preferred.

The moldings may be lined either with or without a fiber-reinforcing material, and/or else fiber-reinforcing material may additionally be added to the blend of the invention and/or to the mixture of the invention. The fiber-reinforcing materials may therefore be woven fabrics, uniaxial and multiaxial laid fabrics, nonwovens, and short fibers of the following fiber materials: glass fibers, carbon fibers, aramid fibers, PE fibers (Dyneema), and basalt fibers. Preference is given to woven fabrics and to uniaxial and multiaxial lays of glass fibers and carbon fibers. In the case of large components which are fiber-reinforced, the components are preferably lined with the fiber-reinforcing material. Uniaxial and multiaxial lays of glass fibers are particularly preferred. The rotor shells for wind turbines are preferably lined with laid glass fiber fabrics.

The moldings are produced preferably by the process of the invention, in which a corresponding mold is provided, the blend of the invention is introduced into this mold, and the blend is cured to completion only when the mold has been completely filled. In the case of the process of the invention, the blend of the invention, which may comprise the mixture of the invention, is introduced into the corresponding mold preferably by way of the infusion technology. In this case a vacuum is applied to the molding. This vacuum draws the blend comprising epoxy resin and the mixture of the invention into the mold under suction at temperatures below the initial curing temperature, and so the viscosity during the filling operation remains virtually unchanged and all of the regions of the molding are filled by the blend before the latter is fully cured. This is followed by complete curing of the blend in the molding. For complete curing it is possible to apply further heat sources from outside.

In the presence of epoxy resins, the mixture of the invention can also be used as a structural adhesive for composite components with one another and also with other materials of construction such as metals and concrete. In this context the mixture of the invention or the blend of the invention can be combined with fibrous fillers such as short glass fibers and with fillers such as thixotropic agents (hydrophilic and hydrophobic fumed silicas), UV stabilizers (nanoscale oxides such as titanium dioxide and zinc oxide), flame retardants (polyphosphates and phosphorus), silicates and carbonates. In relation to the prior art, the structural adhesives combine a long processing life with short curing times under the curing conditions specified above.

EXAMPLES

A prior art used was a commercially available infusion resin system used for years for producing rotor blades of wind turbines.

The resin (Epikote Resin MGS RIM 135 from Hexion) comprises bisphenol A diglycidyl ether and 1,6-hexanediol diglycidyl ether.

The hardener (Epikure Curing Agent MGS RIMH 1366 from Hexion) comprises alkyl ether amine, aminoethylpiperazine, isophoronediamine, benzyl alcohol, and nonylphenol.

The composition of the blend used in the experiments below is as follows:

The epoxy resin comprises 78% by weight of commercial bisphenol A bisglycidyl ether (Epilox A 19-03) and 22% by weight of butanediol bisglycidyl ether (Epilox P13-21).

The mixture of the invention for curing the epoxy resin comprises 60% by weight of Polyetheramine D230, 25% by weight of isophoronediamine, and 15% by weight of tetramethylguanidine.

The processing parameters of the epoxy resin system (epoxy resin and mixture of the invention) were determined by means of rheological measurements (MCR 301 Anton Paar) and are shown in Table 1.

TABLE 1

Processing parameters

|  | Inventive blend ○ | Prior art □ |
|---|---|---|
| Mixing viscosity 30° C. (DIN 53019) | 200 mPa·s | 210 mPa·s |
| Mixing viscosity 40° C. (DIN 53019) | 115 mPa·s | 110 mPa·s |
| Viscosity increase 40° C. to 1 Pas (DIN 16945) | 152 min | 85 min |

Figure 1:
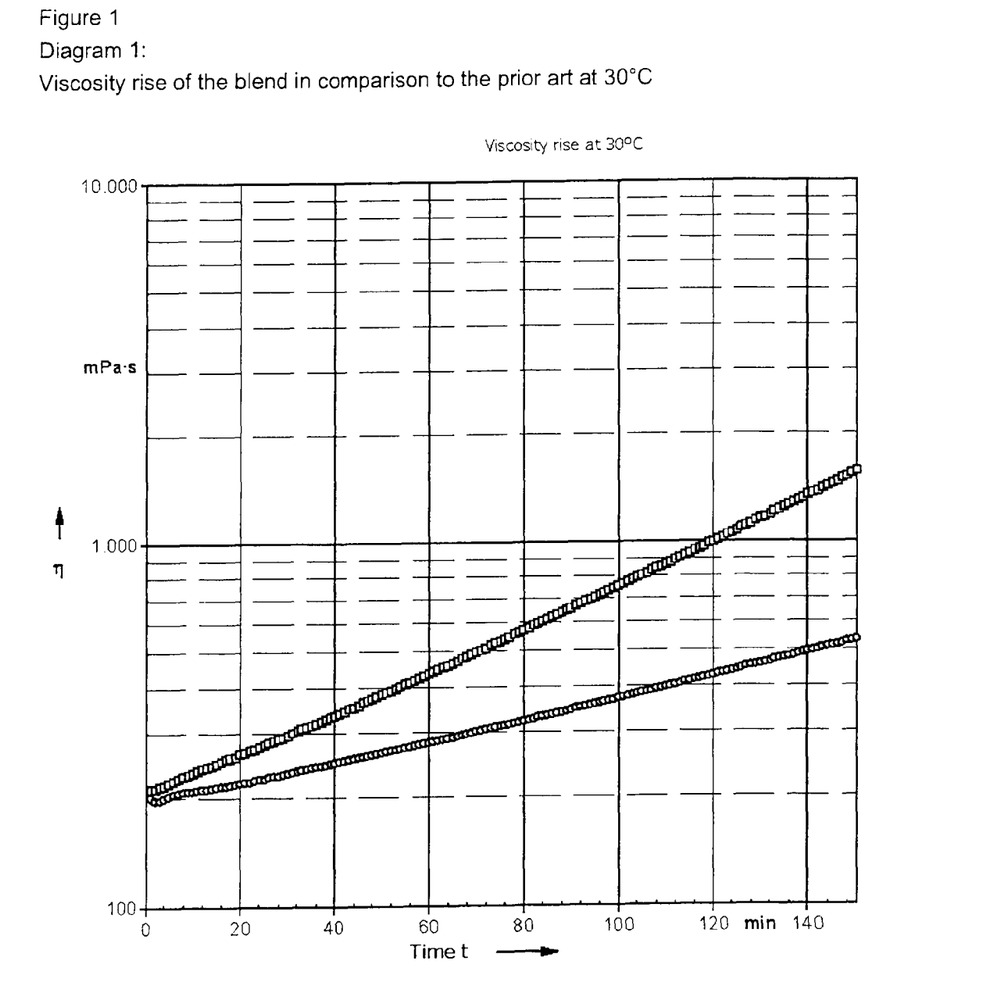
FIG. 1: A diagram showing the change in viscosity as a function of time at 30° C. for the inventive blend (○) and the prior art (□).

The time within which the blend can be processed in the VARTM process with a viscosity of below 1 Pas is significantly longer than for the prior art. The change in viscosity as a function of time is shown graphically in diagram 1 (FIG. 1).

| Inventive blend ○ | D-PP25-SNO; [d = 1 mm] | ○ η viscosity |
| Prior art □ | D-PP25-SNO; [d = 1 mm] | □ η viscosity |

Alternatively, for the blend in comparison to the prior art, the infusion temperature selected can be higher, which, via a lower viscosity because of the temperature, leads to a reduced infusion time.

A longer processing life or more rapid infusion is not per se a significant improvement on the prior art if a consequence thereof is a prolongation of the cure time.

However, the mixture of the invention can be activated by a corresponding temperature regime, and so combines a long processing life with a short cure time:

The blend comprising epoxy resin and the mixture of the invention possesses a latency which means that, at the processing temperatures, the rise in viscosity is slow.

However, when the temperature is raised in order to cure the components, there is an increase in the reactivity above the reactivity of the prior art.

As a result of a corresponding temperature regime (processing temperature=20° C.-50° C. and curing temperature=55° C.-90° C.), this means that the overall cycle time can be reduced, and the processing life can even be extended. As a result there is an increase in the operational stability.

Figure 2:
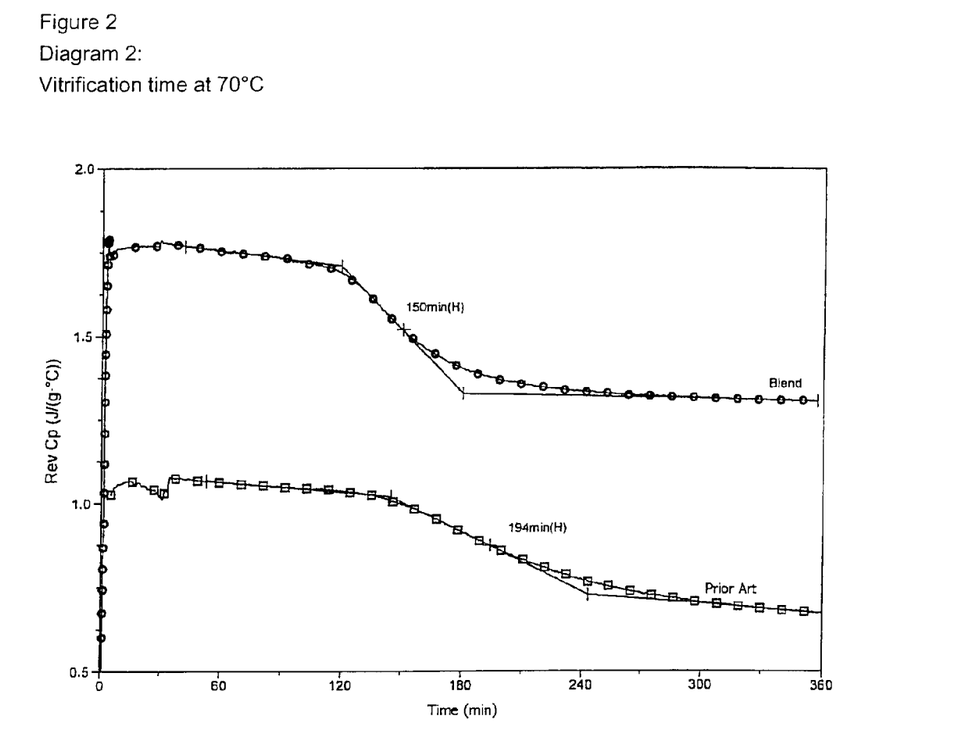
FIG. 2: A diagram showing the vitrification time as a function of time at 70° C. for inventive blend (○) and the prior art (□).

One method of estimating the cycle time is to determine the vitrification time. For this measurement, using a differential scanning calorimeter (DSC), the specific heat capacity is determined as a function of time at a constant temperature (75° C. in the example). There is a change in the specific heat capacity on transition from liquid (vitreous) to solid, which is seen as a step in the corresponding diagram. The results of the comparison with the prior art are shown in diagram 2 (FIG. 2).

The blend attains this transition point about 25% earlier than the standard system.

In order to confirm these findings, pure resin plaques were investigated after 2 h, 3 h, 4 h, 5 h and 6 h of curing at 70° C. For each sample plaque, a DSC sample was cured in parallel in the oven and subjected to measurement thereafter. For the pure resin plaques, both tensile characteristics and flexural characteristics were ascertained.

The 4 mm pure resin plaques were cast in aluminum molds (wall thickness 6 mm) at room temperature and placed in a thermal oven at 70° C. After the times indicated in the table, the mold was then removed and the sample plaque was demolded. The characteristics of the cured moldings are shown in Table 2.

TABLE 2

Mechanical characteristics of the pure resin samples for different curing conditions

| | Curing conditions: | | | | |
|---|---|---|---|---|---|
| | 120 min 70° C. | 180 min 70° C. | 240 min 70° C. | 300 min 70° C. | 360 min 70° C. |
| Glass transition temperature (ISO 11357-2) | 78° C. | 81° C. | 82° C. | 82° C. | 84° C. |
| Elasticity modulus (ISO 527-2) | 3.5 GPa | 3.3 GPa | 3.1 GPa | 3.2 GPa | 3.0 GPa |
| Tensile strength (ISO 527-2) | 72 MPa | 69 MPa | 70 MPa | 71 MPa | 71 MPa |
| Elongation at Fmax (ISO 527-2) | 3.40% | 4.10% | 5.00% | 4.80% | 5.20% |
| Flexural strength (ISO 178) | 122 MPa | 117 MPa | 117 MPa | 117 MPa | 117 MPa |
| Elongation at Fmax (ISO 178) | 4.70% | 5.40% | 6.00% | 5.90% | 6.10% |

In summary it can be stated that this blend, comprising an epoxy resin and the mixture of the invention, attains its ultimate mechanical properties after 4-6 h at 70° C. In contrast, in the technical datasheets for other epoxy resin systems (prior art), there are indications such as 8 h at 80° C. in respect of recommended curing conditions.

The invention claimed is:

1. A process for producing a molding, the process comprising:
   (I) introducing, into a mold, a blend comprising
      (A) an epoxy resin, and
      (B) a mixture comprising
         i) a first hardener component comprising an amine (a1) having a functionality ≥2, and
         ii) from 5 to 30% by weight, based on a total weight of the mixture, of a second hardener component, which is a compound of formula (I):

(I)

wherein R1, R2, and R3 each independently stand for an organic radical comprising 1 to 20 C. atoms and hydrogen, and R4 is an organic radical comprising 1 to 20 C. atoms or a group —C(NH)NR5R6, wherein R5 and R6 each independently stand for an organic radical comprising 1 to 20 C. atoms and hydrogen; and then,
   (II) curing the blend in the mold,
      wherein the blend contains 0.4 to 0.9 amine equivalent, per equivalent of epoxide of the epoxy resin present in the blend, of the amine (a1) of the first hardener component, which when mixed stoichiometrically with the epoxy resin in a 100 g batch, has a cure time of less than 24 h at room temperature.

2. The process of claim 1, wherein the mold and/or the blend in comprises a reinforcing material, the blend penetrating the reinforcing material and/or being mixed with it.

3. The process of claim 1, wherein the amine (a1) of the first hardener component is a polyetheramine having a functionality ≥2, and
   wherein the first hardener component further comprises a second amine (a2), which is a further amine having a functionality ≥2.

4. The process of claim 1, wherein, in formula (I):
   R1, R2, and R3 are each hydrogen, methyl, ethyl, n-propyl, isopropyl, n-butyl, sec-butyl, phenyl, or o-tolyl; and
   R4 is methyl, ethyl, n-propyl, isopropyl, n-butyl, sec-butyl, phenyl, o-tolyl, or a group —C(NH)NR5R6-, wherein R5 and R6 are each independently hydrogen, methyl, ethyl, n-propyl, isopropyl, n-butyl, sec-butyl, phenyl, or o-tolyl.

5. The process of claim 3, wherein the amine (a1) of the first hardener component is a polyetheramine having a functionality ≥2 selected from the group consisting of: 3,6-dioxa-1,8-octanediamire; 4,7,10-trioxa-1,13-tridecanediamine; 4,7-dioxa-1,10-decanediamine; 4,9-dioxa-1,12-docecanediamine; polyetheramine based on triethylene glycol with an average molar mass of 148; difunctional, primary polyetheramine prepared by aminating an ethylene glycol grafted with propylene oxide, with an average molar mass of 176; difunctional, primary polyetheramine based on propylene oxide with an average molar mass of 4000; difunctional, primary polyetheramine prepared by aminating a polyethylene glycol grafted with propylene oxide, with an average molar mass of 2003; aliphatic polyetheramine based on polyethylene glycol grafted with propylene oxide, with an average molar mass of 900; aliphatic polyetheramine based on polyethylene glycol grafted with propylene oxide, with an average molar mass of 600; difunctional, primary polyetheramine prepared by aminating a diethylene glycol grafted with propylene oxide, with an average molar mass of 220; aliphatic polyetheramine based on a copolymer of poly(tetramethylene ether glycol) and polypropylene glycol with an average molar mass of 1000; aliphatic polyetheramine based on a copolymer of poly(tetramethylene ether glycol) and polypropylene glycol with an average molar mass of 1900; aliphatic polyetheramine based on a copolymer of poly(tetramethylene ether glycol) and polypropylene glycol with an average molar mass of 1400; polyethertriamine based on an at least trihydric alcohol grafted with butylene oxide, with an average molar mass of 400; aliphatic polyetheramine prepared by aminating alcohols grafted with butylene oxide, with an average molar mass of 219; polyctheramine based on pentaerythritol and propylene oxide with an average molar mass of 600; difunctional, primary polyetheramine based on polypropylene glycol with an average molar mass of 2000, difunctional; primary polyetheramine based on polypropylene glycol with an average molar mass of 230; difunctional, primary polyetheramine based on polypropylene glycol with an average molar mass of 400; trifunctional, primary polyctheramine prepared by reacting propylene oxide with trimethylolpropane, followed by amination of the terminal OH groups, with an average molar mass of 403; trifunctional, primary polyetheramine prepared by reacting propylene oxide with glycerol, followed by amination of the terminal OH groups, with an average molar mass of 5000; and a polyetheramine having an average molar mass of 400, prepared by aminating polyTHF which has an average molar mass of 250,
   wherein the amine (a2) of the first hardener component is an amine having a functionality ≥2 selected from the group consisting of 1,12-diaminododecane, 1,10-diaminodecane, 1,2-diaminocyclohexane, 1,2-propanediamine, 1,3-bis(aminomethyl)cyclohexane, 1,3-propanediamine, 1-methyl-2,4-diaminocyclohexane, 2,2'-oxybis(ethylamine), 3,3'-dimethyl-4,4'-diaminodicyclohexylmethane, 4,4'-methylenedianiline, 4-ethyl-4-methylamino-1-octylamine, diethylenetriamine, ethylenediamine, methylenediamine, isophoronediamine, menthenediamine, xylylenediamine, N-aminoethylpiperazine, neopentanediamine, norbornanediamine, octane-ethylenediamine, piperazine, 4,8-diaminotricyclo[5.2.1.0]decane, tolylenediamine, triethylenetetramine, trimethyihexamethylenediamine, and
   wherein a weight ratio of the amine (a1) of the first hardener component to the amine (a2) of the first hardener component is from 0.1 to 10:1.

6. The process of claim 3, wherein the amine (a1) of the first hardener component is a polyetheramine having a functionality of ≥2 selected from the group consisting of: difunctional, primary polyetheramine prepared by aminating a diethylene glycol grafted with propylene oxide, with an average molar mass of 220; aliphatic polyetheramine based on polyethylene glycol grafted with propylene oxide, with an average molar mass of 900; aliphatic polyetherarnine based on a copolymer of poly(tetramethylene ether glycol) and polypropylene glycol, with an average molar mass of 1000; aliphatic polyetheramine based on a copolymer of poly(tetramethylene ether glycol) and polypropylene glycol, with an average molar mass of 1900; aliphatic polyetheramine based on a copolymer of poly(tetramethylene ether glycol) and polypropylene glycol, with an average molar mass of 1400; polyethertriamine based on an at least trihydric alcohol grafted with butylene oxide, with an average molar mass of 400; aliphatic polyetheramine prepared by aminating alcohols grafted with butylene oxide, with an average molar mass of 219; difunctional, primary polyetheramine based on polypropylene glycol, with an average molar mass of 230; difunctional, primary polyetheramine based on polypropylene glycol, with an average molar mass of 400; trifunctional, primary polyetheramine prepared by reacting propylene oxide with trimethylolpropane, followed by amination of the terminal OH groups, with an average molar mass of 403; and polyetheramine based on propylene oxide and glycerol with an average molar mass of 5000.

7. The process of claim 3, wherein the amine (a1) of the first hardener component is a polyetheramine selected from the group consisting of polyetheramine D 230, polyetheramine D 400, polyetheramine T 403, and polyetheramine T 5000,
  wherein the amine (a2) of the first hardener component is an amine selected from the group consisting of isophoronediamine, aminoethylpiperazine, 1,3bis(aminomethyl)cyclohexarie, and triethylenetetramine, and
  wherein the second hardener component is tetramethylguanidine.

8. The process of claim 7, wherein the introduction into the mold comprises infusion technology.

* * * * *